United States Patent

Dickoré et al.

[11] 4,348,331
[45] Sep. 7, 1982

[54] PROCESS FOR THE PREPARATION OF N-SUBSTITUTED IMIDO-DICARBOXYLIC ACID DIARYL ESTERS

[75] Inventors: Karlfried Dickoré, Leverkusen; Engelbert Kühle, Berg.-Gladbach, both of Fed. Rep. of Germany

[73] Assignee: Bayer Aktiengesellschaft, Leverkusen, Fed. Rep. of Germany

[21] Appl. No.: 233,249

[22] Filed: Feb. 10, 1981

[30] Foreign Application Priority Data

Sep. 19, 1980 [DE] Fed. Rep. of Germany ....... 3035392
Sep. 19, 1980 [DE] Fed. Rep. of Germany ....... 3035393

[51] Int. Cl.$^3$ ............... C07C 125/073; C07C 125/075
[52] U.S. Cl. .................... 260/465 D; 260/465.4; 560/22; 560/25; 560/115; 560/134; 560/137; 549/426; 549/493
[58] Field of Search ................ 560/137, 158, 25, 22, 560/115, 134; 260/465 D, 465.4, 345.8 R, 347.4

[56] References Cited

U.S. PATENT DOCUMENTS

| | | | |
|---|---|---|---|
| 1,527,868 | 2/1925 | Hautman | 560/158 |
| 2,395,750 | 2/1946 | Muskat | 560/25 |
| 2,522,393 | 9/1950 | Milone | 560/25 |
| 2,541,646 | 2/1951 | Gleim | 560/158 |
| 3,555,076 | 1/1971 | Thoma | 560/137 |
| 4,014,923 | 3/1977 | Kuhle | 560/137 |
| 4,056,527 | 11/1977 | Schlee | 544/194 |

FOREIGN PATENT DOCUMENTS

| | | | |
|---|---|---|---|
| 38-768 | 2/1963 | Japan | 560/25 |
| 484683 | 5/1938 | United Kingdom . | |
| 1054673 | 1/1967 | United Kingdom | 560/134 |

OTHER PUBLICATIONS

Houben-Weyl, "Methoden der organischen Chemie", 1952, 4, Auflage, Band VIII: Sauerstoffverbindungen III.

Primary Examiner—Michael L. Shippen
Attorney, Agent, or Firm—Felfe & Lynch

[57] ABSTRACT

This invention relates to a process for the preparation of N-substituted imido-dicarboxylic acid diaryl ester compound of the formula $$R^1-N(CO-OR^2)_2 \quad (I)$$

wherein
$R^1$ is an optionally substituted aliphatic, cycloaliphatic, araliphatic, aromatic or heterocyclic radical, and
$R^2$ is an optionally substituted aryl radical, which can be used as intermediates for the production of known herbicides, which process comprises reacting an amine salt of the formula $$R^1-NH_2.HX^1 \quad (II)$$

wherein $X^1$ is a halogen, with a carbonic acid aryl ester halide of the formula $$R^2-O-CO-X^2 \quad (III)$$

wherein $X^2$ is halogen, at a temperature from 100° C. to 300° C.

32 Claims, No Drawings

PROCESS FOR THE PREPARATION OF N-SUBSTITUTED IMIDO-DICARBOXYLIC ACID DIARYL ESTERS

This invention relates to a process for the preparation of N-substituted imido-dicarboxylic acid diaryl eater compounds, more specifically, to a single stage process for such preparation. The ester compounds produced are valuable intermediates for the synthesis of herbicidally active compounds.

The present invention now provides a process for the production of an dicarboxylic acid diaryl ester of the general formula $$\text{ti } R^1\text{-N(CO-OR}^2)_2 \tag{I}$$

in which
  $R^1$ represents an optionally substituted aliphatic, cycloaliphatic, araliphatic, aromatic or heterocyclic radical and
  $R^2$ represents an optionally substituted aryl radical,
in which an amine salt of the general formula $$R^1\text{-NH}_2.HX^1 \tag{II}$$

in which
  $R^1$ has the abovementioned meaning and
  $X^1$ represents a halogen atom,
is reacted with a carbonic acid aryl ester halide of the general formula $$R^2O\text{-CO-}X^2 \tag{III}$$

in which
  $R^2$ has the abovementioned meaning and
  $X^2$ represents a halogen atom,
at a temperature between 100° and 300° C.

It is to be regarded as surprising that the reaction according to the invention proceeds, since amine salts do not react with carbonic acid ester halides at low temperatures, and, in the presence of an acid-binding agent, the free amines give only the N-substituted carbamic acid aryl esters. It was also to be expected that, at elevated temperature, re-splitting of the N-substituted carbamic acid aryl esters formed in the first stage would take place (see Houben-Weyl, Methoden der org. Chemie (Methods of organic Chemistry), 4th edition, volume 8, page 127 (1952)).

If neopentylamine hydrochloride and carbonic acid phenyl ester chloride are used as starting substances, the course of the reaction for the production of compounds of the present invention is illustrated by the following equation:

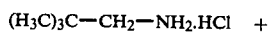

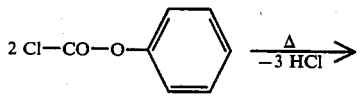

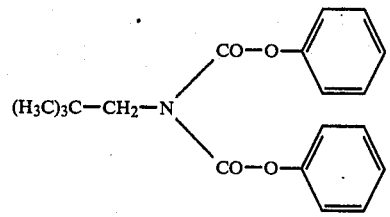

Preferred amine salts to be used as starting substances are those of formula (II) in which $R^1$ represents a straight-chain or branched alkyl radical which has 1 to 10 carbon atoms and is optionally substituted by lower alkoxy, lower alkylmercapto, halogen (in particular chlorine or fluorine), cyano or nitro; an alkenyl radical with 3 to 8 carbon atoms; an alkynyl radical with 3 to 8 carbon atoms; a cycloaliphatic radical which has 3 to 8 ring carbon atoms and is optionally substituted by lower alkyl; an araliphatic radical with a total of 7 to 12 carbon atoms, it being possible for the aromatic ring system optionally to be substituted by halogen, nitro, trifluoromethyl, cyano, lower alkyl and/or lower alkoxy; an aromatic radical which has 6 to 12 carbon atoms and is optionally substituted by halogen, nitro, trifluoromethyl, cyano, lower alkyl and/or lower alkoxy, or a heterocyclic radical with 5 or 6 ring atoms and 1 to 3 hetero-atoms, such as oxygen, sulphur and/or nitrogen, in the ring, and $X^1$ represents a fluorine, chlorine or bromine atom, preferably a chlorine atom. The expressions "lower alkyl", "lower alkoxy" and "lower alkylmercapto" in the context of this invention are intended to denote appropriate radicals with in each case 1 to 4 carbon atoms.

The primary amines which can be used according to the invention and on which the amines salts (II) are based are all known from the literature (see for example, Houben-Weyl, Methoden der Organischen Chemie (Methods of Organic Chemistry), 4th edition, volume XI/1, pages 9 to 1,033 (1957)). The hydrogen halide acid salts can be prepared from the amines by known processes, by addition of the corresponding hydrogen halide.

Specific examples which may be mentioned of the primary amines on which the hydrohalides of the formula (II) are based are: methylamine, ethylamine, propylamine, isopropylamine, 1,1-dimethyl-propylamine, 1,2-dimethylpropylamine, 2,2-dimethyl-propylamine (neopentylamine), 1,2,2-trimethyl-propylamine, 1-ethyl-propylamine, 1-isopropyl-2-methyl-propylamine, butylamine, isobutylamine, sec.-butylamine, tert.-butylamine, 1-methyl-butylamine, 2,2-dimethyl-butylamine, 3,3-dimethyl-butylamine, 1,3,3-trimethyl-butylamine, pentylamine, 1-methyl-pentylamine, 2,2-dimethyl-pentylamine, 1,2,2-trimethyl-pentylamine, hexylamine, 2-ethyl-hexylamine, 1-methyl-octylamine, allylamine, 2-methylallylamine, propargylamine, cyclopropylamine, cyclopropylmethylamine, cyclobutylamine, cyclopentylamine, cyclopentyl-methylamine, cyclohexylamine, cyclohexylmethylamine, 3-methyl-cyclohexylamine, 4-methylcyclohexylamine, 4-tert.-butyl-cyclohexylamine, 4-methylcyclohexyl-methylamine, 3,3,5-trimethyl-cyclohexylamine, cyclohex-3-enyl-methylamine, 3,4-dimethyl-cyclohex-3-enylamine, cyclohex-3-enyl-methylamine, 3,4-dimethylcyclohex-3-enyl-methylamine, cycloheptanylamine, cycloheptanyl-methylamine, cyclooctanylamine, cyclooctanylmethylamine, cyclododecanylamine, cyclododecanyl-methylamine, adamantyl-methylamine, 2-(bicyclo[2.2.1]heptyl)methylamine, 6-(2,3,3a,4,5,6,7,7a-octahydro-4,7-methanoindenyl-methylamine, 2-(1,2,3,4,5,6,7,8,8a,4a-decahydro-1,4:5,8-dimethanonaphthyl)-methylamine, 5-(4,5,6,7,7a,3a-hexahydro-indenyl)-methylamine, 2-chloro-ethylamine, 2,2,2-trifluoro-ethylamine, 3,3-dichloro-3-fluoro-propylamine, 3,3,3-trifluoro-propylamine, 2,2-difluoro-propylamine, 2,2,2-trifluoro-1-methyl-ethylamine, 6-chlorohexylamine, 3-trifluoromethyl-cyclohexylamine, 4-trifluoromethyl-cyclohexylamine, 3-trifluoromethyl-cyclohexyl-methylamine, 4-trifluoromethyl-cyclohexyl-methylamine, 2-methoxy-ethylamine, 3-methoxy-propylamine, 5-cyano-pentylamine, 2-ethoxycarbonyl-ethylamine, aniline, 2-chloroaniline, 3-chloroaniline, 4-chloroaniline, 2,4-dichloroaniline, 3,4-dichloroaniline, 3,5-dichloroaniline, 2,4,5-trichloroaniline, 3-nitroaniline, 4-nitroaniline, 3-chloro-4-nitroaniline, 2-methylaniline, 2-chloro-6-methylaniline, 4-chloro-2-trifluoromethylaniline, 3-methylaniline, 3-trifluoromethylaniline, 4-methylaniline, 2,6-dimethylaniline, 2-ethylaniline, 2-ethyl-6-methylaniline, 2,6-diethylaniline, benzylamine, 1-phenyl-ethylamine, 2-phenyl-ethylamine, 2-chloro-benzylamine, 2,4-dichloro-benzylamine, fur-2-yl-methylamine, tetrahydrofur-2-yl-methylamine, tetrahydro-pyran-2-yl-methylamine and tetrahydro-pyran-3-yl-methylamine.

Preferred carbonic acid aryl ester halides also to be used as starting substances are those of formula (III) in which $R^2$ represents a phenyl or naphthyl radical which is optionally substituted by chlorine, methyl and/or methoxy, and $X^2$ represents a chlorine or fluorine atom, it being possible for the radicals $X^1$ and $X^2$ to be identical or different.

The carbonic acid aryl ester halides of the formula (III) which can be used according to the invention are known, or they can be prepared by known processes. Thus, for example, the carbonic acid phenyl ester chlorides can be prepared in a manner which is in itself known, by phosgenation of phenols (see Houben-Weyl, Methoden der organischen Chemie (Methods of Organic Chemistry), 4th Edition, Volume 8, page 103 (1952)); the corresponding carbonic acid phenyl ester fluorides can be obtained analogously from phenols and difluorophosgene (see J. Chem. Soc. [London] 1948, page 2183).

Specific examples of starting compounds of the formula (III) which may be mentioned are: the carbonic acid ester chlorides of phenol, 4-chlorophenol, 4-cresol and 1-naphthol and the carbonic acid ester fluoride of phenol. A particularly preferred combination of starting compounds of formula (II) and (III) is neopentylamine hydrochloride and carbonic acid phenyl ester chloride.

The reaction according to the invention can be carried out in the absence or in the presence of a diluent. If no diluent is used, it is most expedient for the amine hydrohalide of formula (II) to be introduced or uniformly metered, with a screw device, in portions into the carbonic acid aryl ester halide of formula (III), which is in the reaction vessel and has been warmed to the reaction temperature.

Possible diluents for the carbonic acid aryl ester halide of formula (III), which is in general initially introduced, are high-boiling inert organic solvents, such as chlorinated or nitrated aromatic hydrocarbons (for example chlorobenzene, dichlorobenzenes, trichlorobenzenes or nitrobenzenes).

It is also possible, and in many cases particularly advantageous, to carry out the reaction in an excess of the carbonic acid aryl ester halide of formula (III) used as a reactant.

If the reaction according to the invention is carried out in the presence of an inert organic solvent as the diluent, in general 2 to 15 moles, preferably 3 to 12 moles, of a carbonic acid aryl ester halide of the formula (III) are employed per mole of an amine salt of the formula (II). In contrast, if an excess of carbonic acid halide (III) is used as the diluent, up to 20 moles, but appropriately about 4 to 15 moles and preferably about 8 to 12 moles, of carbonic acid aryl ester halide (III) can be employed per mole of amine salt of the formula (II). It is thus advisable for the carbonic acid aryl ester halide of formula (III) in all cases to be employed in amounts which are greater than the stoichiometric amount.

The process according to the invention is carried out without the addition of an acid-binding agent. However, it has proved advantageous for the hydrogen halide formed in the course of the reaction to be removed rapidly from the reaction mixture. This is most appropriately achieved by passing a continuous stream of air or nitrogen through the reaction mixture (see the Preparative Examples).

The reaction temperatures can be varied within the substantial range, as indicated above, of between 100° and 300° C., preferably between 170° and 250° C.

The reaction according to the invention is in general carried out under normal pressure.

The reaction products are isolated in a simple manner by separating the reaction mixture by distillation. Solid, higher-melting imido-dicarboxylic acid diaryl esters can also be easily purified by recrystallization.

The N-substituted imido-dicarboxylic acid diaryl esters of formula (I) which can be prepared according to the invention can be used as intermediate products for the preparation of known herbicidal active compounds from the 1,3,5-triazine-2,4-(1H,3H)-dione series (see, for example, DE-OS (German Published Specification) 2,254,200 and U.S. Pat. No. 4,056,527).

According to a process which has not hitherto belonged to the state of the art (and which is the subject of copending U.S. Ser. No. 233,250, filed Feb. 10, 1981. 1,3,5-triazine-2,4-(1H,3H)-diones of the formula

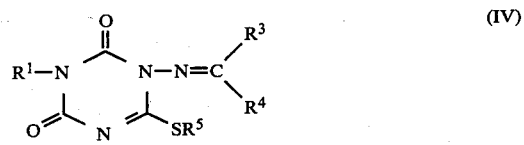

in which
$R^1$ has the abovementioned meaning and
$R^3$, $R^4$ and $R^5$ in each case represent identical or different alkyl radicals, can be prepared with a high yield and purity when the N-substituted imido-dicarboxylic acid diaryl esters according to the invention, of the general formula

in which $R^1$ and $R^2$ have the abovementioned meaning, are reacted with an isothiosemicarbazone of the general formula

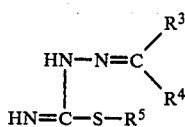
(V)

in which $R^3$, $R^4$ and $R^5$ have the abovementioned meaning, in approximately stoichiometric amounts, without using a diluent and without adding a base as an auxiliary, at temperatures between 50° and 150° C., preferably between 70° and 120° C.

The triazinediones of formula (IV) can be worked up and isolated, for example, by a procedure in which the (optionally substituted) phenol formed in the condensation reaction—(I)+(V)→(IV)—is distilled off in vacuo and the residue is purified, if necessary, by distillation under a high vacuum or by recrystallization.

The 1,3,5-triazine-2, 4(1H,3H)-diones of formula (IV) thus prepared are themselves herbicidal active compounds; however, they can also be easily converted into the corresponding 1-amino-1,3,5-triazine-2, 4(1H,3H)-diones of the general formula

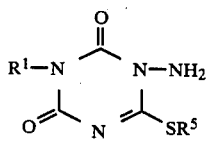
(VI)

in which $R^1$ and $R^5$ have the abovementioned meaning, which are likewise excellent herbicides, by hydrolytic splitting off of the alkylidene radical ($=CR^3R^4$) which serves as a protective group. Furthermore, the S-alkyl radicals ($-SR^5$) in compounds of formulae (IV) and (VI) can be replaced by alkylamino or dialkylamino groups by reaction with primary or secondary amines, herbicidal active compounds which are also known being obtained (see likewise DE-OS (German Published Specification) 2,254,200 and U.S. Pat. No. 4,056,527).

The new process given here for the preparation of the herbicidal active compounds of the general formulae (IV) and (VI) and 6-amino derivatives thereof, in which the imido-dicarboxylic acid diaryl esters of formula (I) according to the invention are used as starting compounds, has considerable and surprising advantages compared with the processes already known, for example from DE-OS (German Published Specification) 2,254,200. Thus, the cyclization reaction can be carried out in the melt of the starting materials without using solvents. No other auxiliaries, such as organic bases, are required in this procedure. The only by-products are phenols (no hydrogen halides being produced), which can easily be separated off and re-used. Finally, the imido-dicarboxylic acid diaryl esters of formula (I) employed as starting substances can be prepared in high yields in an industrially simple manner from readily accessible precursors by the process claimed in the above-mentioned copending patent application.

The isothiosemicarbazones of the general formula (V) are known or they can be prepared by known processes, for example by S-alkylation of thiosemicarbazones (see Houben-Weyl, Methoden der organischen Chemie (Methods of Organic Chemistry), 4th Edition, Volume 9, page 912).

The synthesis of the particularly effective herbicidal active compound 1-amino-6-ethylthio-3-neopentyl-1,3,5-triazine-2, 4(1H,3H)-dione of formula (VIa) (see for example, Danish Pat. No. 136,067), starting from the compound N-neopentylamido-dicarboxylic acid diphenyl ester of formula (Ia) according to the invention, is described below by way of example; the course of the reaction can be represented by the following equation:

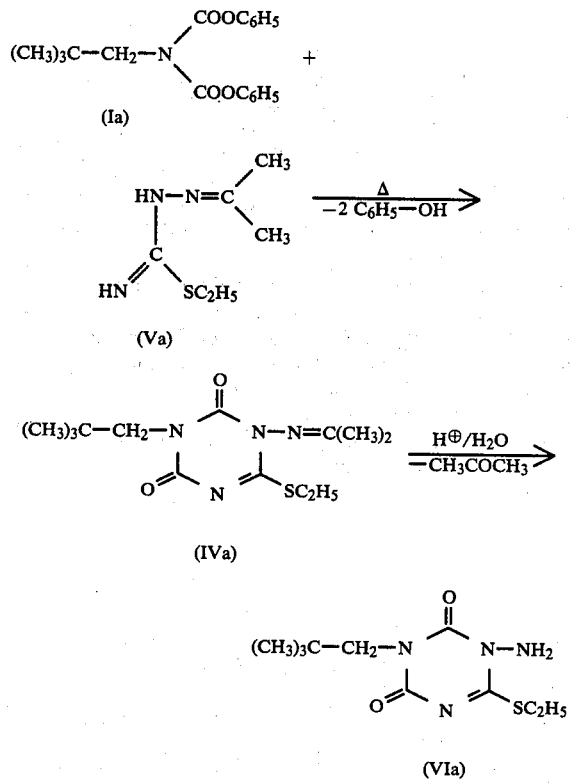

A mixture of 65.4 g (0.2 mole) of N-neopentylimidodicarboxylic acid diphenyl ester (see Preparative Example 1) and 31.8 g (0.2 mole) of acetone S-ethylisothiosemicarbazone of formula (Va) is melted and the melt is stirred at 100° C. for 5 hours. The phenol formed is then distilled off in vacuo. The residue, which essentially consists of 1-isopropylideneamino-6-ethylthio-3-neopentyl-1,3,5-triazine-2, 4(1H,3H)-dione of formula (IVa), is dissolved in 200 ml of isopropanol. To split off the isopropylidene protective group hydrolytically, 2.8 g of p-toluenesulphonic acid are added, and 14.4 ml of water are added dropwise at a temperature of 60° C. and under a pressure of 200–300 mbar in the course of half an hour. The acetone formed is distilled off during the reaction, together with about 100 ml of isopropanol. The 1-amino-6-ethylthio-3-neopentyl-1,3,5-triazine-2, 4(1H,3H)-dione of formula (VIa) which has crystallized out is filtered off at 0° C. and washed with methanol. 38.2 g of the compound of formula (VIa) of melting point 202° C. are obtained, corresponding to a yield of 74% of theory.

Herbicidally active 1-amino-3-isobutyl-6-methylthio-1,3,5-triazine-2, 4(1H,3H)-dione of formula (VIb), which is known (see, for example, Danish Pat. No. 136,067), can be prepared in an analogous manner starting from the compound N-isobutyl-imido-dicarboxylic acid diphenyl ester of formula (Ib) according to the invention, it being possible for the intermediate product 1-isopropylidene-amino-3-isobutyl-6-methylthio-1,3,5-triazine-2, 4(1H,3H)-dione of formula (IVb) to be isolated:

1st stage

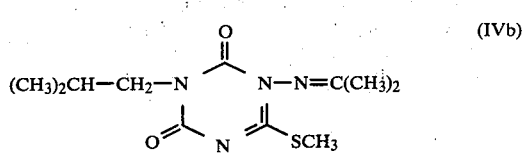

34.6 g (0.11 mole) of N-isobutyl-imido-dicarboxylic acid diphenyl ester of formula (IB) (see Preparative Example 5) and 16.0 g (0.11 mole) of acetone S-methylisothiosemicarbazone are melted at 50° C. and the melt is stirred for 4 hours in an oil bath of 100° C. The phenol formed is distilled off under a pressure of 18 mbars, the bath temperature being increased to 140° C. The residue (30.3 g) solidifies; it is boiled up with 150 ml of cyclohexane, 22.4 g of pure 1-isopropylideneamino-3-isobutyl-6-methylthio-1,3,5-triazine-2,4(1H,3H)-dione of formula (IVb) of melting point 125°–127° C. remaining as undissolved material. A further 6.4 g of the compound of formula (IVb) crystallize from the filtrate of the mixture. The total yield is 28.8 g (97% of theory). The compound of formula (IVb) can be distilled: boiling point: 165° C. under 0.38 mbar.

2nd stage

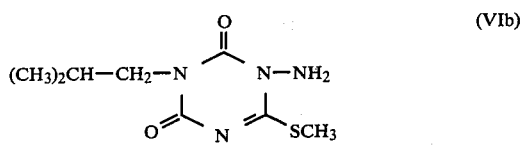

27.0 g (0.1 mole) of the compound of formula (IVb) are dissolved in 200 ml of isopropanol at 60° C. in a distillation apparatus and a pressure of 260–200 mbars is established, so that the solvent starts to boil and is condensed in the descending condenser. The internal temperature is 45°–50° C. A solution of 0.4 ml of concentrated sulphuric acid in 7 ml of water is then added dropwise in the course of 15 minutes, about 70 ml of isopropanol, together with the acetone formed, being distilled off during this period. 14.5 g of 1-amino-3-isobutyl-6-methylthio-1,3,5-triazine-2, 4(1H,3H)-dione of formyl (VIb) of melting point 167°–169° C. crystallize out, at 0° C., from the solution which remains; a further 4.5 g are obtained from the concentrated filtrate of the mixture. The total yield of 19.0 g corresponds to 83% of theory.

The Preparative Examples which follow to illustrate the process of the present invention in more detail.

PREPARATIVE EXAMPLES

Example 1

$$(CH_3)_3C—CH_2—N(CO—O—C_6H_5)_2 \quad (I)$$

810 ml (6.4 moles) of carbonic acid phenyl ester chloride were heated to the boiling point in a 2 liter four-necked flask, and 123.5 g (1 mole) of neopentylamine hydrochloride were metered in by means of a screw device in the course of 2–3 hours, while stirring and passing through nitrogen. The mixture was then subsequently stirred at the boiling point for a further 6 hours.

Analysis of this reaction solution by gas chromatography gave the following values, without taking into consideration the carbonic acid phenyl ester chloride employed in excess: 10.7% of neopentyl isocyanate, 20.1% of diphenyl carbonate, 63.3% of N-neopentyl-imido-dicarboxylic acid diphenyl ester (I) and 4.0% of orthocarbonic acid tetraphenyl ester.

The reaction solution obtained was worked up by distillation.

After distilling off the excess carbonic acid phenyl ester chloride under a waterpump vacuum (boiling point 75° C. under 16 mbars), the diphenyl carbonate was distilled off under a high vacuum at a bath temperature of 140°–150° C.

The residue which remained consisted of 96% pure N-neopentyl-imido-dicarboxylic acid diphenyl ester. Yield: 238 g (70% of theory). A sample recrystallized from petroleum ether melted at 81° C. The boiling point was 156° C. under 0.02 mbar.

The neopentylamine hydrochloride required as the starting material could be prepared as follows:

40 g of hydrogen chloride gas were passed into a solution of 87 g (1 mole) of neopentylamine in 500 ml of toluene, while stirring, and the product was filtered off and dried at 150° C. in a drying cabinet. 120 g (97% of theory) of neopentylamine hydrochloride were obtained in the form of a fine powder with a melting point of 300° C.

The compounds of the general formula (I) listed in the following table could be prepared in an analogous manner:

TABLE $R^1—N(CO—OR^2)_2$ (I)

| Example No. | $R^1$ | $R^2$ | Melting point (°C.) | Boiling point (°C./mbar) |
|---|---|---|---|---|
| 2 | $CH_3—$ | $—C_6H_5$ | 102–105 | |
| 3 | $(CH_3)_2CH—$ | $—C_6H_5$ | 35–37 | 155/0.07 |
| 4 | $C_2H_5—CH—$<br>$\quad\quad\,\,|$<br>$\quad\quad CH_3$ | $—C_6H_5$ | | 165–170/0.2 |
| 5 | $(CH_3)_2CH—CH_2—$ | $—C_6H_5$ | 40 | 160/0.1 |
| 6 | $(CH_3)_3C—$ | $—C_6H_5$ | 132 | 150/0.1 |
| 7 | $(CH_3)_3C—CH_2—$ | 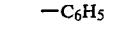 | 71–73 | 172/0.008 |

TABLE-continued $$R^1-N(CO-OR^2)_2 \quad (I)$$

| Example No. | $R^1$ | $R^2$ | Melting point (°C.) | Boiling point (°C./mbar) |
|---|---|---|---|---|
| 8 | (CH₃)₃C—CH₂— | —C₆H₄—Cl | 72–73 | 182/0.03 |
| 9 | (CH₃)₃C—CH₂— | naphthyl | 92–93 | |
| 10 | C₂H₅—C(CH₃)₂— | —C₆H₅ | 95–97 | 150/0.05 |
| 11 | (CH₃)₃C—CH(CH₃)— | —C₆H₅ | 40–42 | 159/0.15 |
| 12 | C₂H₅—C(CH₃)₂—CH₂— | —C₆H₅ | 49–50 | 178/0.05 |
| 13 | [(CH₃)₂CH—]₂CH— | —C₆H₅ | | 158–161/0.02 |
| 14 | C₄H₉—CH(C₂H₅)—CH₂ | —C₆H₅ | | 182–185/0.06 |
| 15 | C₇H₁₅—CH(CH₃)— | —C₆H₅ | | 173/0.09 |
| 16 | (C₂H₅)₂CH— | —C₆H₅ | 54–56 | 140/0.12 |
| 17 | CH₂=CH—CH₂— | —C₆H₅ | | 153/0.04 |
| 18 | cyclopentyl | —C₆H₅ | 53 | 160/0.1 |
| 19 | cyclohexyl | —C₆H₅ | 85 | 175/0.09 |
| 20 | (CH₃)₃C—cyclohexyl— | —C₆H₅ | | 186–200/0.001 |
| 21 | H₃C—cyclohexyl—CH₂— | —C₆H₅ | | 185–188/0.06 |
| 22 | cyclohexenyl—CH₂— | —C₆H₅ | | 195–200/0.09 |
| 23 | 2,6-dimethylcyclohexenyl—CH₂— | —C₆H₅ | | 200–205/0.07 |
| 24 | methylcyclo— | —C₆H₅ | 57–62 | 210/0.6 |
| 25 | cyclo—CH₂— | —C₆H₅ | | 240–250/0.1 |
| 26 | norbornyl—CH₂— | —C₆H₅ | 84–86 | 202/0.02 |

TABLE-continued

| Example No. | $R^1$ | $R^2$ | Melting point (°C.) | Boiling point (°C./mbar) |
|---|---|---|---|---|
| 27 | (norbornyl)-CH₂— | —C₆H₅ | 92–94 | |
| 28 | (norbornyl)-CH₂— | —C₆H₅ | | 232–240/0.07 |
| 29 | (norbornenyl)-CH₂— | —C₆H₅ | | 215–220/0.07 |
| 30 | Cl(CH₂)₂— | —C₆H₅ | | 177–190/0.1 |
| 31 | F₃C—CH₂— | —C₆H₅ | 76 | 140/0.3 |
| 32 | Cl₂FC—(CH₂)₂— | —C₆H₅ | 68–70 | 187/0.008 |
| 33 | F₃C—(CH₂)₂— | —C₆H₅ | 66–69 | 147–153/0.3 |
| 34 | CH₃—CF₂—CH₂— | —C₆H₅ | 60–62 | 160–164/0.08 |
| 35 | F₃C—CH(CH₃)— | —C₆H₅ | | 150/0.17 |
| 36 | Cl—(CH₂)₆— | —C₆H₅ | | 210/0.1 |
| 37 | H₃C—O—(CH₂)₂— | —C₆H₅ | | 168/0.1 |
| 38 | H₃C—O—(CH₂)₃— | —C₆H₅ | | 168–170/0.08 |
| 39 | NC—(CH₂)₅— | —C₆H₅ | | 230–235/0.1 |
| 40 | C₂H₅—O—CO—(CH₂)₂— | —C₆H₅ | | 190–193/0.08 |
| 41 | C₆H₅— | —C₆H₅ | 124–125 | |
| 42 | 2,4-dichlorophenyl | —C₆H₅ | 97–100 | |
| 43 | 3,5-dichlorophenyl | —C₆H₅ | 178–180 | |
| 44 | C₆H₅—CH₂— | —C₆H₅ | 70–72 | 191/0.01 |
| 45 | furfuryl-CH₂— | —C₆H₅ | | 190–200/0.1 |
| 46 | tetrahydropyranyl-CH₂— | —C₆H₅ | 78–79 | 176/0.007 |

It will be understood that the specification and examples are illustrative, but not limitative, of the present invention and that other embodiments within the spirit and scope of the invention will suggest themselves to those skilled in the art.

What is claimed is:

1. Process for the production of an N-substituted imido-dicarboxylic acid diaryl ester compound of the formula $$R^1\text{-N(CO-OR}^2)_2 \qquad (I)$$

wherein $R^1$ is a straight-chain or branched alkyl of from 1 to 10 carbon atoms; substituted alkyl wherein the substituents are at least one of lower alkoxy, lower alkylmercapto, halogen, cyano or nitro; alkenyl or alkynyl of from 3 to 8 carbon atoms; cycloaliphatic of from 3 to 8 carbon atoms; substituted by cycloaliphatic wherein the substituent is lower alkyl; araliphatic with from 7 to 12 carbon atoms; substituted araliphatic wherein the aromatic ring system is substituted by halogen, nitro, trifluoromethyl, cyano, lower alkyl or lower alkoxy; an aromatic radical of from 6 to 12 carbon atoms and is optionally substituted by halogen, nitro, trifluoromethyl, cyano, lower alkyl or lower alkoxy;

$R^2$ is a phenyl or naphthyl radical; substituted phenyl or naphthyl wherein the substituents are at least one of chlorine, methyl or methoxy; and which process comprises reacting an amine salt of the formula $$R^1\text{-}NH_2HX^1 \qquad (I)$$

in which

R$^1$ is defined as above; and
X$^1$ is a chlorine atom with a carbonic acid aryl ester halide of the formula $$R^2O\text{---}CO\text{---}X^2 \qquad (III)$$

wherein

R$^2$ is defined as above; and
X$^2$ is a chlorine or fluorine atom at a temperature from 100° C. to 300° C.

2. Process as claimed in claim 1 wherein the reaction is carried out at a temperature of between 170° and 250° C.

3. Process as claimed in claim 1 wherein the reaction is carried out in the presence of a diluent.

4. Process as claimed in claim 1 wherein the carbonic acid aryl ester halide of formula (III) is employed in a greater than stoichiometric amount.

5. Process as claimed in claim 1 wherein R$^1$ is alkyl of from 1 to 10 carbon atoms.

6. Process as claimed in claim 1 wherein R$^1$ is substituted alkyl, wherein the substituents are selected from the group consisting of lower alkoxy, lower alkylmercapto, halogen, cyano or nitro.

7. Process as claimed in claim 1 wherein R$^1$ is alkenyl or alkynyl with from 3 to 8 carbon atoms.

8. Process as claimed in claim 1 wherein R$^1$ is cycloaliphatic with from 3 to 8 carbon atoms.

9. Process as claimed in claim 1 wherein R$^1$ is substituted cycloaliphatic wherein the substituents are selected from lower alkyl.

10. Process as claimed in claim 1 wherein R$^1$ is an araliphatic radical with from 7 to 12 carbon atoms.

11. Process as claimed in claim 1 wherein R$^1$ is a substituted araliphatic radical wherein the aromatic ring is substituted by halogen, nitro, trifluoromethyl, cyano, lower alkyl and lower alkoxy.

12. Process as claimed in claim 1 wherein R$^1$ is an aromatic radical of from 6 to 12 carbon atoms.

13. Process as claimed in claim 1 wherein R$^1$ is a substituted aromatic radical wherein the substituents are selected from the group consisting of halogen, nitro, trifluoromethyl, cyano, lower alkyl and lower alkoxy.

14. Process as claimed in claim 1 wherein R$^2$ is phenyl.

15. Process as claimed in claim 1 wherein R$^2$ is a substituted phenyl wherein the substituents are at least one of chlorine, methyl or methoxy.

16. Process as claimed in claim 1 wherein R$^2$ is naphthyl.

17. Process as claimed in claim 1 wherein R$^2$ is substituted naphthyl wherein the substituents are at least one of chlorine, methyl or methoxy.

18. Process as claimed in claim 1 wherein neopentylamine hydrochloride is reacted with carbonic acid phenyl ester chloride.

19. Process as claimed in claim 1 wherein sec.-butylamine hydrochloride is reacted with carbonic acid phenyl ester chloride.

20. Process as claimed in claim 1 wherein isobutylamine hydrochloride is reacted with carbonic acid phenyl ester chloride.

21. Process as claimed in claim 1 wherein neopentylamine hydrochloride is reacted with carbonic acid tolyl ester chloride.

22. Process as claimed in claim 1 wherein 2-aminohexane hydrochloride is reacted with carbonic acid phenyl ester chloride.

23. Process as claimed in claim 1 wherein 2,2-dimethyl-1-aminobutane hydrochloride is reacted with carbonic acid phenyl ester chloride.

24. Process as claimed in claim 1 wherein 2,4-dimethyl-3-aminopentane hydrochloride is reacted with carbonic acid phenyl ester chloride.

25. Process as claimed in claim 1 wherein 2-ethyl-hexylamine hydrochloride is reacted with carbonic acid phenyl ester chloride.

26. Process as claimed in claim 1 wherein 3-aminopentane hydrochloride is reacted with carbonic acid phenyl ester chloride.

27. Process as claimed in claim 1 wherein 3-amino-1-propylene hydrochloride is reacted with carbonic acid phenyl ester chloride.

28. Process as claimed in claim 1 wherein cyclopentylamine hydrochloride is reacted with carbonic acid phenyl ester chloride.

29. Process as claimed in claim 1 wherein cyclohexylamine hydrochloride is reacted with carbonic acid phenyl ester chloride.

30. Process as claimed in claim 1 wherein 2-(bicyclo[2.2.1]-heptyl)-methylamine hydrochloride is reacted with carbonic acid phenyl ester chloride.

31. Process as claimed in claim 1 wherein 2,2,2-trifluoroethylamine hydrochloride is reacted with carbonic acid phenyl ester chloride.

32. Process as claimed in claim 1 wherein 1,1,1-trifluoro-2-aminopropane hydrochloride is reacted with carbonic acid phenyl ester chloride.

* * * * *